United States Patent [19]

Murib et al.

[11] 4,271,081
[45] Jun. 2, 1981

[54] PROCESS FOR THE PREPARATION OF TETRAHYDROFURAN

[75] Inventors: Jawad H. Murib; John M. Inskeep, both of Cincinnati, Ohio

[73] Assignee: National Distillers and Chemical Corp., New York, N.Y.

[21] Appl. No.: 159,978

[22] Filed: Jun. 16, 1980

[51] Int. Cl.$^3$ ............................................. C07D 307/08
[52] U.S. Cl. ................................................. 260/346.11
[58] Field of Search .................................... 260/346.11

[56] References Cited

U.S. PATENT DOCUMENTS 3,931,238  1/1976  Starks ............................... 260/346.11

*Primary Examiner*—Richard Raymond
*Attorney, Agent, or Firm*—Kenneth D. Tremain

[57] ABSTRACT

Tetrahydrofuran is prepared by reacting a 1,4-dihalobutane such as 1,4-dichlorobutane with water in the presence of a strong acid. The product tetrahydrofuran can be recovered, for example, by distillation.

16 Claims, No Drawings

PROCESS FOR THE PREPARATION OF TETRAHYDROFURAN

This application relates to subject matter disclosed in commonly assigned copending U.S. patent application Ser. Nos. 159,979 and 159,977 filed of even date herewith, respectively entitled "Process for the Preparation of Glycols" and "Process for the Preparation of Tetrahydrofuran".

BACKGROUND OF THE INVENTION

1. Field of the Invention

This invention relates to tetrahydrofuran, and in particular, relates to the manufacture of tetrahydrofuran from 1,4-dihalobutane.

2. Description of the Prior Art

Tetrahydrofuran is a cyclic ether finding wide and substantial use as a solvent for natural and synthetic resins, especially the vinyl resins, in coatings, adhesives, printing inks, as a chemical intermediate and as a monomer. Tetrahydrofuran has been prepared via the catalytic hydrogenation of furan, from the reaction of acetylene and formaldehyde and from the dehydrocyclization of 1,4-butanediol or dehydrochlorocyclization of 4-chloro-1-butanol. The last mentioned cyclization processes are of particular interest since they employ as starting materials aliphatic derivatives which are relatively abundant and inexpensive (viz., U.S. Pat. Nos. 2,950,232; 3,467,679; 3,726,905; 4,002,646; and 4,093,633). Heretofore, no attempt has been made to utilize the 1,4-dihalobutanes as starting materials for conversion to tetrahydrofuran since these compounds would first have to be converted to 4-chloro-1-butanol or 1,4-butanediol preparative to the cyclization to the cyclic ether.

SUMMARY OF THE INVENTION

It has now been surprisingly discovered that if a 1,4-dihalobutane is reacted with water in the presence of a strong acid, tetrahydrofuran is produced. Thus, in accordance with the present invention, a process is provided for preparing tetrahydrofuran which comprises reacting a 1,4-dihalobutane with water in the presence of a catalytically effective amount of strong acid.

While not wishing to be bound in any way, it would appear that the aforesaid reaction at first converts the 1,4-dihalobutane to the corresonding glycol, 1,4-butanediol, by hydrolysis and the 1,4-butanediol thereafter cyclizes to tetrahydrofuran. Regardless of the actual mechanism or reaction sequence by which 1,4-dihalobutanes are converted to tetrahydrofuran in accordance with this invention, it remains that the starting compounds herein can be employed as a source for this commercially important cyclic ether without having to proceed through a series of distinct reactions each requiring a separate operation. Accordingly, the process of this invention provides a simple route to tetrahydrofuran utilizing inexpensive and readily available raw materials.

DESCRIPTION OF THE PREFERRED EMBODIMENTS

Among the 1,4-dihalobutanes which can be used herein with good results are included 1,4-dichlorobutane, 1,4-dibromobutane, 1-chloro-4-bromobutane, 1-chloro-4-iodobutane, and the like. The 1,4-dihalobutanes can be used singly or in admixture. 1,4-dichlorobutane is especially preferred herein due to its relatively low cost and ready availability.

The reaction of the 1,4-dihalobutane and water can be carried out with less than the stoichiometrically required amount of water but it is generally preferable to use a large stoichiometric excess of water, e.g., from about 1.5 to about 10 times the amount calculated.

It is desirable to carry out the hydrolysis reaction in the presence of a phase transfer agent or an emulsifying agent to facilitate the hydrolysis and shorten the reaction time. Phase transfer agents useful in the hydrolysis include alkali metal tetraaryl boron compounds, e.g., sodium tetraphenyl boron, quaternary ammonium or phosphonium salts in which the anion is halide, hydroxide, sulfate, bisulfate, phosphate, and the like. Suitable emulsifying agents include fatty acid salts of Group 1A metals, and the like.

Optionally, the hydrolysis reaction can be carried out in any inert solvent which will dissolve the 1,4-dihalobutane and which is miscible with water. Such solvents include cyclic ethers such tetrahydrofuran, dioxane and tetrahydropyran; ethers such as methyl ethers of ethylene glycols; ketones such as acetone; lactones of hydroxy organic acids such as butyrolactone; organic acids; monoalcohols; glycols such as ethylene glycol and 1,3-propylenediol; and the like. Where it is desirable to use a mutual solvent system for the 1,4-dihalobutane and water, it is generally preferred to employ tetrahydrofuran as the solvent for the sake of convenience and simplicity.

The reaction conditions are not overly critical in that wide ranges of temperature and pressures are operable. The practical limitations of production equipment will dictate to a great extent the selection of temperatures and pressure at which the reaction is to be effected. Thus, using available production systems, the selected temperature should be at least about 20° C. and can range up to about 350° C. and even higher. For most purposes, the preferred operating temperature ranges from about 100° to about 250° C. The pressure can range from somewhat below atmospheric to as high as 160 atmospheres. Most desirably, the pressure should be in the range of from about atmospheric to about 50 atmospheres, particularly when employing the aforesaid preferred temperature range.

The catalyst for the hydrolysis reaction herein is a strong acid. The term "strong acid" as used herein embraces organic and inorganic acids which are highly dissociated in water. Such acids are well known in the art and include hydriodic acid, sulfuric acid, sulfonic acid, especially the arylsulfonic acids, phosphoric acid, phosphonic acid, especially the arylphosphonic acids, and the like. Strong inorganic acids such as hydriodic acid, sulfuric acid and phosphoric acid are particularly advantageous for use as catalysts herein. The amount of strong acid catalyst employed does not seem to be critical and can vary considerably. At least a catalytically effective amount of catalyst should be used, of course. In general, an amount of catalyst which is effective to provide a reasonable reaction rate is sufficient. In practice, an amount of strong acid in the range of from about 0.001 to about 0.1 moles, and preferably from about 0.002 to about 0.025 moles, per mole of 1,4-dihalobutane, provides good results.

Recovery of the product tetrahydrofuran can be accomplished by any of the known and routine techniques, e.g., distillation.

The amount of time required for conversion of the 1,4-dihalobutane to tetrahydrofuran will vary according to the specific reaction conditions and in general, is on the order of from about 0.5 to about 12 hours. Optimum yields of tetrahydrofuran for a given set of reaction conditions can be readily determined employing known and conventional techniques as, for example, chromatographic analysis.

The following examples are further illustrative of the process of this invention for the preparation of tetrahydrofuran.

EXAMPLE 1

The following were charged to a three-neck round bottom flask provided with a high speed mixer, a nitrogen inlet and temperature control:
3.0 ml 1,4-dichlorobutane
24.0 ml water
0.15 ml sodium lauryl sulfate
0.30 hydriodic acid (57% by weight)

The reaction medium was blanketed with nitrogen and heated to from 100°–105° C. with constant mixing. After a reaction period of four hours, analysis of the reaction medium indicated the presence of 1,4-butanediol. The following day, re-analysis of the reaction medium indicated the absence of 1,4-butanediol and the presence of tetrahydrofuran.

EXAMPLE 2

Employing the same apparatus sand procedure of Example 1, the flask was charged with the following:
3.0 ml 1,4-dichlorobutane
24.0 ml water
0.30 ml hydriodic acid (57% by weight)

After six hours of reaction, analysis showed the reaction medium to contain 1,4-butanediol. Re-analysis approximately 75 minutes later indicated a slight reduction in 1,4-butanediol. The following day, further re-analysis of the reaction medium indicated the absence of 1,4-butanediol and the presence of tetrahydrofuran.

EXAMPLE 3

Employing the same apparatus and procedure as in Example 1, the flask was charged with the following:
3.0 ml 1,4-dichlorobutane
24.0 ml water
0.30 ml hydriodic acid (57% by weight)

After a reaction period of four hours, analysis showed the presence of 1,4-butanediol. The reaction was continued for several additional hours and re-analysis of the reaction medium showed that the 1,4-butanediol had converted to tetrahydrofuran.

EXAMPLE 4

A mixture of 11.9 g 1,4-dichlorobutane (82% purity), 30 g of water and 1 ml of concentrated sulfuric acid as catalyst was heated in a shaking Hastelloy reactor (2.5 cm inside diameter×13.8 cm deep) at 170° C. for 8 hours. Upon cooling, the reaction mixture was found to contain 3.54 g of tetrahydrofuran (by chromatography). Mass spectral analysis gave cracking patterns identical to that of an authentic sample of tetrahydrofuran.

EXAMPLE 5

Example 1 was repeated except 1 ml of 85% $H_3PO_4$ was used as catalyst instead of sulfuric acid. The reaction mixture contained 3.39 g of tetrahydrofuran.

EXAMPLE 6

A mixture of 3.39 g 1,4-dichlorobutane (82%), 24 g water and 0.3 g aqueous hydriodic acid (57%) as catalyst was placed in a 125 ml 3-neck round bottom flask (pyrex) equipped with a high speed stirrer, condenser and a serum cap for sample withdrawal. The reaction waas heated at reflux for 4 hours. Analysis of the mixture showed that the product was tetrahydrofuran.

EXAMPLE 7

A mixture of 11.3 g 1,4-dichlorobutane (82%), 20 g water, 0.25 ml aqueous hydriodic acid (57%) as catalyst and 0.2 g tetradecyltrimethylammonium bromide was placed in a 125 ml 3-neck round bottom flask equipped with a high speed stirrer, condenser and a serum cap for sample withdrawal. The reaction was heated at reflux for 1 hour. The distillate formed two layers, both of which contained tetrahydrofuran.

EXAMPLE 8

A mixture of 63.5 g 1,4-dischlorobutane (82%), 18 g water, 3.0 ml aqueous hydriodic acid (57%) as catalyst and 0.5 g hexadecyltributylphosphonium bromide was placed in a 125 ml 3-neck round bottom flask equipped with a high speed stirrer, condenser and a serum cap for sample withdrawal. The reaction was heated at reflux for 1 hour. The fraction collected at 75° C. was rich in THF.

EXAMPLE 9

Example 7 is repeated except that 0.2 g sodium tetraphenyl boron is used as the transfer agent in place of tetradecyltrimethylammonium bromide. The product contained tetrahydrofuran.

What is claimed is:

1. A process for preparing tetrahydrofuran which comprises reacting a 1,4-dihalobutane with water in the presence of a catalytically effective amount of strong acid to provide tetrahydrofuran.

2. The process of claim 1 wherein the 1,4-dihalobutane is 1,4-dichlorobutane.

3. The process of claim 1 wherein a phase transfer agent is employed.

4. The process of claim 3 wherein the phase transfer agent is a quaternary ammonium or phosphonium salt.

5. The process of claim 3 wherein the phase transfer agent is tetradecyltrimethylammonium bromide.

6. The process of claim 3 wherein the phase transfer agent is tetradecyltributylphosphonium bromide.

7. The process of claim 1 wherein an emulsifying agent is employed.

8. The process of claim 7 wherein the emulsifying agent is a fatty acid salt of a metal from Group 1A.

9. The process of claim 7 wherein the emulsifying agent is sodium lauryl sulfate.

10. The process of claim 1 wherein water is present in stoichiometric excess.

11. The process of claim 1 wherein the temperature of the reaction medium is from about 20° C. to about 350° C.

12. The process of claim 11 wherein the temperature of the reaction medium is from about 100° C. to about 250° C.

13. The process of claim 1 wherein the pressure of the reaction is from below atmospheric to about 160 atmospheres.

14. The process of claim 13 wherein the pressure of the reaction is from atmospheric to about 50 atmospheres.

15. The process of claim 1 wherein the strong acid is hydriodic acid, sulfuric acid or phosphoric acid.

16. The process of claim 1 wherein from about 0.001 to about 0.1 moles of acid are employed.

* * * * *